United States Patent
Blumberg, Jr. et al.

(10) Patent No.: US 10,872,685 B2
(45) Date of Patent: Dec. 22, 2020

(54) ELECTRONIC PATIENT MONITORING SYSTEM

(71) Applicant: DEKA Products Limited Partnership, Manchester, NH (US)

(72) Inventors: David Blumberg, Jr., Deerfield, NH (US); Dean Kamen, Bedford, NH (US); Marc J. Gorayeb, Hampton, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 13/971,258

(22) Filed: Aug. 20, 2013

(65) Prior Publication Data

US 2013/0339049 A1 Dec. 19, 2013

Related U.S. Application Data

(63) Continuation of application No. 13/011,543, filed on Jan. 21, 2011, now abandoned.

(60) Provisional application No. 61/297,544, filed on Jan. 22, 2010.

(51) Int. Cl.
*G16H 20/10* (2018.01)
*G16H 20/40* (2018.01)
*G06Q 50/24* (2012.01)

(52) U.S. Cl.
CPC ............. *G16H 20/10* (2018.01); *G06Q 50/24* (2013.01); *G16H 20/40* (2018.01)

(58) Field of Classification Search
CPC ............................... G06Q 50/22; G06Q 50/24
USPC ....................................................... 705/2–3
See application file for complete search history.

(56) References Cited

U.S. PATENT DOCUMENTS

| | | | |
|---|---|---|---|
| 3,658,445 A | 4/1972 | Pulman |
| 4,696,671 A | 9/1987 | Epstein |
| 4,877,034 A | 10/1989 | Atkins |
| 4,939,689 A | 7/1990 | Davis |
| 5,041,086 A | 8/1991 | Koenig |
| 5,207,642 A | 5/1993 | Orkin |
| 5,317,506 A | 5/1994 | Coutre |
| D348,101 S | 6/1994 | Poli |
| 5,368,562 A | 11/1994 | Blomquist |
| 5,482,446 A | 1/1996 | Williamson |
| 5,485,408 A | 1/1996 | Blomquist |

(Continued)

FOREIGN PATENT DOCUMENTS

| AU | 659233 B2 | 5/1995 |
|---|---|---|
| AU | 738474 B2 | 9/2001 |

(Continued)

OTHER PUBLICATIONS

AAMI and FDA, Infusing Patients Safely: Priority Issues from the AAMI/FDA Infusion Device Summit, Symposium, Oct. 5-6, 2010, pp. 1-48, AAMI, Arlington, VA, USA.

(Continued)

*Primary Examiner* — Eliza A Lam
(74) *Attorney, Agent, or Firm* — James D. Wyninegar, Jr.

(57) ABSTRACT

An electronic patient monitoring system comprising a monitoring client and a remote communicator are provided. The monitoring client is configured to store patient information. The patient information may be patient-specific information. The monitoring client may receive the information from a database, e.g., through a monitoring server.

33 Claims, 7 Drawing Sheets

(56) References Cited

U.S. PATENT DOCUMENTS

| | | | |
|---|---|---|---|
| 5,527,289 A | 6/1996 | Foster | |
| 5,537,618 A | 7/1996 | Boulton | |
| 5,713,856 A | 2/1998 | Eggers et al. | |
| 5,719,761 A | 2/1998 | Gatti | |
| 5,781,442 A | 7/1998 | Engleson et al. | |
| 5,836,910 A | 11/1998 | Duffy | |
| 5,937,353 A * | 8/1999 | Fapojuwo | H04W 36/04 455/439 |
| 5,941,846 A | 8/1999 | Duffy | |
| 5,961,487 A | 10/1999 | Davis | |
| 6,021,392 A | 2/2000 | Lester | |
| 6,024,539 A | 2/2000 | Blomquist | |
| 6,139,495 A | 10/2000 | De La Huerga | |
| 6,255,951 B1 | 7/2001 | De La Huerga | |
| 6,267,559 B1 | 7/2001 | Mossman et al. | |
| 6,308,171 B1 | 10/2001 | De La Huerga | |
| 6,314,384 B1 | 11/2001 | Goetz | |
| 6,315,720 B1 | 11/2001 | Williams | |
| 6,317,719 B1 | 11/2001 | Schrier | |
| 6,319,200 B1 | 11/2001 | Lai | |
| 6,327,570 B1 | 12/2001 | Stevens | |
| 6,346,886 B1 | 2/2002 | De La Huerga | |
| 6,348,777 B1 | 2/2002 | Brown | |
| 6,398,727 B1 | 6/2002 | Bui | |
| 6,408,330 B1 | 6/2002 | DeLaHuerga | |
| 6,421,650 B1 | 7/2002 | Goetz | |
| 6,427,088 B1 | 7/2002 | Bowman, IV | |
| 6,519,569 B1 | 2/2003 | White et al. | |
| 6,554,798 B1 | 4/2003 | Mann | |
| 6,579,242 B2 | 6/2003 | Bui | |
| 6,668,196 B1 | 12/2003 | Villegas et al. | |
| 6,671,563 B1 | 12/2003 | Engelson | |
| 6,694,334 B2 | 2/2004 | DuLong | |
| 6,745,764 B2 | 6/2004 | Hickle | |
| 6,775,577 B2 | 8/2004 | Crnkovich | |
| 6,790,198 B1 | 9/2004 | White et al. | |
| 6,880,034 B2 | 4/2005 | Manke | |
| 6,976,349 B2 | 12/2005 | Baldwin | |
| 6,985,870 B2 | 1/2006 | Martucci et al. | |
| 6,993,402 B2 | 1/2006 | Klass et al. | |
| 7,039,878 B2 | 5/2006 | Auer | |
| 7,096,072 B2 | 8/2006 | Engleson et al. | |
| 7,103,419 B2 | 9/2006 | Engleson | |
| 7,107,106 B2 | 9/2006 | Engleson | |
| 7,117,041 B2 | 10/2006 | Engleson | |
| 7,161,484 B2 | 1/2007 | Tsoukalis | |
| 7,165,221 B2 | 1/2007 | Monteleone | |
| 7,171,277 B2 | 1/2007 | Engleson et al. | |
| 7,216,802 B1 | 5/2007 | De La Huerga | |
| 7,236,936 B2 | 6/2007 | White et al. | |
| 7,300,418 B2 | 11/2007 | Zaleski | |
| 7,302,266 B1 * | 11/2007 | Sill | H04W 72/048 370/331 |
| 7,303,549 B2 | 12/2007 | Flaherty | |
| 7,379,885 B2 | 5/2008 | Zakim | |
| 7,384,410 B2 | 6/2008 | Eggers et al. | |
| 7,433,853 B2 | 10/2008 | Brockway et al. | |
| 7,452,190 B2 | 11/2008 | Bouton et al. | |
| 7,471,994 B2 | 12/2008 | Ford et al. | |
| 7,539,593 B2 | 5/2009 | Machacek | |
| 7,565,301 B2 | 7/2009 | Moubayed | |
| 7,569,030 B2 | 8/2009 | Lebel | |
| 7,590,551 B2 | 9/2009 | Auer | |
| 7,612,679 B1 | 11/2009 | Fackler | |
| 7,636,718 B1 | 12/2009 | Steen et al. | |
| 7,645,258 B2 | 1/2010 | White et al. | |
| 7,647,237 B2 | 1/2010 | Malave et al. | |
| 7,664,660 B2 | 2/2010 | Korpman | |
| 7,678,071 B2 | 3/2010 | Lebel | |
| 7,685,003 B2 | 3/2010 | Hasan | |
| 7,689,394 B2 | 3/2010 | Furem | |
| 7,693,730 B2 | 4/2010 | Hasan | |
| 7,699,806 B2 | 4/2010 | Ware | |
| 7,703,042 B2 | 4/2010 | Brummel | |
| 7,707,047 B2 | 4/2010 | Hasan | |
| 7,715,277 B2 | 5/2010 | de la Huerga | |
| 7,743,975 B2 | 6/2010 | Miller | |
| 7,771,385 B2 | 8/2010 | Eggers et al. | |
| 7,771,386 B2 | 8/2010 | Eggers et al. | |
| 7,788,369 B2 | 8/2010 | McAllen | |
| 7,813,879 B2 | 10/2010 | Bush | |
| 7,815,602 B2 | 10/2010 | Mann | |
| 7,818,184 B2 | 10/2010 | Penny | |
| 7,819,843 B2 | 10/2010 | Mann | |
| 7,831,446 B2 | 11/2010 | Korpman | |
| 7,835,927 B2 | 11/2010 | Schlotterbeck et al. | |
| 7,839,266 B2 | 11/2010 | Hoglund | |
| 7,850,641 B2 | 12/2010 | Lebel | |
| 7,859,401 B2 | 12/2010 | Falck | |
| 7,860,583 B2 | 12/2010 | Condurso et al. | |
| 7,871,394 B2 | 1/2011 | Halbert | |
| 7,873,489 B2 | 1/2011 | Dolgos | |
| 7,886,231 B2 | 2/2011 | Hopermann | |
| 7,893,876 B2 | 2/2011 | Brown | |
| 7,896,842 B2 | 3/2011 | Palmroos | |
| 7,901,394 B2 | 3/2011 | Ireland | |
| 7,911,353 B2 | 3/2011 | Bedingfield | |
| D636,779 S | 4/2011 | Boush | |
| D636,780 S | 4/2011 | Musleh | |
| 7,933,780 B2 | 4/2011 | De La Huerga | |
| 7,935,076 B2 * | 5/2011 | Estes et al. | 604/65 |
| 7,938,796 B2 | 5/2011 | Moubayed | |
| 7,941,534 B2 | 5/2011 | de la Huerga | |
| 7,942,844 B2 | 5/2011 | Moberg | |
| 7,946,985 B2 | 5/2011 | Mastrototaro | |
| 7,955,289 B2 | 6/2011 | O'Mahony | |
| 7,976,508 B2 | 7/2011 | Hoag | |
| 7,978,564 B2 | 7/2011 | De La Huerga | |
| 8,025,634 B1 | 9/2011 | Moubayed et al. | |
| 8,032,226 B2 | 10/2011 | Miller | |
| 8,038,593 B2 | 10/2011 | Friedman | |
| 8,041,542 B2 | 10/2011 | Pearson | |
| 8,060,381 B2 | 11/2011 | Dyer | |
| 8,073,710 B2 | 12/2011 | Hasan | |
| 8,095,390 B2 | 1/2012 | Bluemler | |
| 8,099,301 B2 | 1/2012 | Keresman, III et al. | |
| 8,126,728 B2 | 2/2012 | Dicks | |
| 8,126,729 B2 | 2/2012 | Dicks | |
| 8,131,565 B2 | 3/2012 | Dicks | |
| 8,131,566 B2 | 3/2012 | Dicks | |
| 8,134,459 B2 | 3/2012 | Smith | |
| 8,149,131 B2 | 4/2012 | Blomquist | |
| 8,152,486 B2 | 4/2012 | Fathallah | |
| 8,178,040 B2 | 5/2012 | Brauer | |
| 8,192,394 B2 | 6/2012 | Estes | |
| 8,214,227 B2 | 7/2012 | Patterson | |
| 8,214,234 B2 | 7/2012 | Hasan | |
| 8,217,946 B2 | 7/2012 | Halpern | |
| 8,219,413 B2 | 7/2012 | Martinez | |
| 8,219,982 B2 | 7/2012 | Harkanyi | |
| 8,222,768 B2 | 7/2012 | Cassidy | |
| 8,225,015 B2 | 7/2012 | Gao-Saari | |
| 8,229,760 B2 | 7/2012 | Hasan | |
| D665,401 S | 8/2012 | Rai | |
| 8,235,938 B2 | 8/2012 | Eggers | |
| 8,239,780 B2 | 8/2012 | Manetta | |
| 8,244,555 B2 | 8/2012 | Masson | |
| 8,255,585 B2 | 8/2012 | Levin | |
| 8,260,635 B2 | 9/2012 | Hasan | |
| 8,271,106 B2 | 9/2012 | Wehba | |
| 8,273,018 B1 | 9/2012 | Fackler | |
| 8,275,576 B2 | 9/2012 | Furem | |
| 8,275,633 B2 | 9/2012 | Baker | |
| 8,291,337 B2 | 10/2012 | Gannin | |
| 8,306,797 B2 | 11/2012 | Furem | |
| 8,308,680 B1 | 11/2012 | Chawla | |
| 8,312,877 B2 | 11/2012 | Elaz | |
| 8,317,752 B2 | 11/2012 | Cozmi | |
| D672,785 S | 12/2012 | Rai | |
| 8,340,792 B2 | 12/2012 | Condurso | |
| 8,352,290 B2 | 1/2013 | Bartz | |
| 8,359,338 B2 | 1/2013 | Butterfield | |
| 8,373,557 B2 | 2/2013 | Smith | |
| 8,380,536 B2 | 2/2013 | Howard | |

(56) References Cited

U.S. PATENT DOCUMENTS

| | | |
|---|---|---|
| 8,414,523 B2 | 4/2013 | Blomquist |
| D682,861 S | 5/2013 | Rounding |
| 8,444,595 B2 | 5/2013 | Brukalo |
| 8,451,230 B2 | 5/2013 | Celentano |
| D694,774 S | 12/2013 | Schuller |
| D701,526 S | 3/2014 | Poston |
| D705,242 S | 5/2014 | Bohmfalk |
| D709,905 S | 7/2014 | Bohmfalk |
| D714,339 S | 9/2014 | Hendrickson |
| 8,938,684 B2 | 1/2015 | Guertler |
| 8,954,336 B2 | 2/2015 | Blomquist |
| D726,752 S | 4/2015 | Angelides |
| D728,601 S | 5/2015 | Angelides |
| D728,779 S | 5/2015 | Sabin et al. |
| D733,724 S | 7/2015 | Kim |
| D735,319 S | 7/2015 | Sabin et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 2001/0031944 A1 | 10/2001 | Peterson et al. |
| 2002/0013538 A1 | 1/2002 | Teller |
| 2002/0184589 A1 | 12/2002 | Eatough |
| 2002/0188465 A1 | 12/2002 | Gogolak et al. |
| 2003/0046110 A1 | 3/2003 | Gogolak |
| 2003/0061073 A1 | 3/2003 | Seow |
| 2003/0106553 A1 | 6/2003 | Vanderveen |
| 2003/0114751 A1 | 6/2003 | Pedain |
| 2003/0135388 A1 | 7/2003 | Martucci et al. |
| 2003/0165128 A1* | 9/2003 | Sisodia ............. H04W 4/00 370/338 |
| 2004/0010425 A1 | 1/2004 | Wilkes et al. |
| 2004/0015132 A1 | 1/2004 | Brown |
| 2004/0147818 A1 | 7/2004 | Levy et al. |
| 2004/0158193 A1 | 8/2004 | Bui et al. |
| 2004/0172283 A1 | 9/2004 | Vanderveen |
| 2004/0193325 A1 | 9/2004 | Bonderud et al. |
| 2004/0193453 A1 | 9/2004 | Butterfield |
| 2005/0022184 A1 | 1/2005 | Birkestrand |
| 2005/0055242 A1 | 3/2005 | Bello et al. |
| 2005/0070767 A1 | 3/2005 | Maschke |
| 2005/0099624 A1 | 5/2005 | Staehr |
| 2005/0144043 A1 | 6/2005 | Holland |
| 2005/0171815 A1 | 8/2005 | Vanderveen |
| 2005/0177096 A1 | 8/2005 | Bollish |
| 2005/0224083 A1 | 10/2005 | Crass et al. |
| 2006/0047538 A1 | 3/2006 | Condurso |
| 2006/0080140 A1 | 4/2006 | Buttner |
| 2006/0095300 A1 | 5/2006 | Schrier |
| 2006/0149140 A1 | 7/2006 | Eldridge |
| 2006/0149591 A1 | 7/2006 | Finn et al. |
| 2006/0184123 A1 | 8/2006 | Gillespie |
| 2006/0258985 A1 | 11/2006 | Russell |
| 2006/0265246 A1 | 11/2006 | Hoag |
| 2007/0061393 A1 | 3/2007 | Moore |
| 2007/0088574 A1 | 4/2007 | Byer et al. |
| 2007/0109325 A1 | 5/2007 | Eveleigh |
| 2007/0136090 A1 | 6/2007 | Loutzenhiser et al. |
| 2007/0191817 A1 | 8/2007 | Martin |
| 2007/0250927 A1 | 10/2007 | Naik |
| 2007/0255250 A1* | 11/2007 | Moberg ............. A61M 5/142 604/503 |
| 2008/0039744 A1 | 2/2008 | Hamilton |
| 2008/0086086 A1* | 4/2008 | Field et al. ................... 604/123 |
| 2008/0091175 A1* | 4/2008 | Frikart et al. ............... 604/891.1 |
| 2008/0097913 A1 | 4/2008 | Dicks |
| 2008/0129496 A1* | 6/2008 | Koblasz ..................... 340/540 |
| 2008/0133265 A1 | 6/2008 | Silkaitis |
| 2008/0140157 A1 | 6/2008 | Goetz |
| 2008/0235765 A1 | 9/2008 | Shimizu |
| 2008/0243055 A1 | 10/2008 | Fathallah et al. |
| 2008/0255438 A1 | 10/2008 | Saidara |
| 2008/0262441 A1 | 10/2008 | Walborn |
| 2009/0069743 A1 | 3/2009 | Krishnamoorthy |
| 2009/0099867 A1 | 4/2009 | Newman |
| 2009/0119330 A1* | 5/2009 | Sampath ............... G16H 10/60 |
| 2009/0150818 A1 | 6/2009 | Bakhreiba |
| 2009/0153058 A1 | 6/2009 | Feng |
| 2009/0153463 A1 | 6/2009 | Arrizza |
| 2009/0153595 A1 | 6/2009 | Cozmi |
| 2009/0157432 A1 | 6/2009 | Palmroos |
| 2009/0183147 A1 | 7/2009 | Davis et al. |
| 2009/0203329 A1 | 8/2009 | White |
| 2009/0216562 A1 | 8/2009 | Faulkner |
| 2009/0234672 A1 | 9/2009 | Dicks |
| 2009/0240526 A1 | 9/2009 | Vesto |
| 2010/0094653 A1 | 4/2010 | Tribble et al. |
| 2010/0114027 A1 | 5/2010 | Jacobson |
| 2010/0130933 A1 | 5/2010 | Holland et al. |
| 2010/0229096 A1 | 9/2010 | Maiocco |
| 2010/0234718 A1 | 9/2010 | Sampath |
| 2010/0257189 A1 | 10/2010 | Campbell |
| 2010/0268157 A1 | 10/2010 | Wehba et al. |
| 2010/0280486 A1 | 11/2010 | Khair et al. |
| 2010/0287006 A1 | 11/2010 | Cannon |
| 2010/0292556 A1 | 11/2010 | Golden |
| 2010/0298662 A1* | 11/2010 | Yu et al. ..................... 600/301 |
| 2011/0004186 A1 | 1/2011 | Butterfield |
| 2011/0105979 A1 | 5/2011 | Schlaeper |
| 2011/0119612 A1 | 5/2011 | Gannon |
| 2011/0153343 A1 | 6/2011 | Tremblay |
| 2011/0167250 A1 | 7/2011 | Dicks |
| 2011/0173704 A1 | 7/2011 | Hanov |
| 2011/0179405 A1 | 7/2011 | Dicks |
| 2011/0184379 A1 | 7/2011 | Van Antwerp |
| 2011/0196306 A1 | 8/2011 | De La Huerga |
| 2011/0205965 A1 | 8/2011 | Sprigg |
| 2011/0224646 A1 | 9/2011 | Yodfat |
| 2011/0231203 A1 | 9/2011 | Rosow |
| 2011/0231204 A1 | 9/2011 | De La Huerga |
| 2011/0241878 A1 | 10/2011 | Hoag |
| 2011/0276605 A1 | 11/2011 | Masson |
| 2011/0282168 A1 | 11/2011 | Weiss |
| 2011/0282688 A1 | 11/2011 | Raggousis |
| 2011/0282691 A1 | 11/2011 | Coffman |
| 2011/0313789 A1 | 12/2011 | Kamen et al. |
| 2011/0320049 A1 | 12/2011 | Chossat |
| 2012/0011253 A1 | 1/2012 | Friedman |
| 2012/0016215 A1 | 1/2012 | Condurso |
| 2012/0016295 A1 | 1/2012 | Tsoukalis |
| 2012/0029300 A1 | 2/2012 | Paquet |
| 2012/0029307 A1 | 2/2012 | Paquet |
| 2012/0029308 A1 | 2/2012 | Paquet |
| 2012/0029309 A1 | 2/2012 | Paquet |
| 2012/0029310 A1 | 2/2012 | Paquet |
| 2012/0029311 A1 | 2/2012 | Raptis |
| 2012/0029312 A1 | 2/2012 | Beaudry |
| 2012/0029314 A1 | 2/2012 | Paquet et al. |
| 2012/0029315 A1 | 2/2012 | Raptis |
| 2012/0029316 A1 | 2/2012 | Raptis |
| 2012/0029941 A1 | 2/2012 | Malave |
| 2012/0030547 A1 | 2/2012 | Raptis |
| 2012/0053533 A1 | 3/2012 | Butterfield |
| 2012/0062387 A1 | 3/2012 | Vik |
| 2012/0065990 A1 | 3/2012 | Howard |
| 2012/0066609 A1 | 3/2012 | Howard |
| 2012/0075061 A1 | 3/2012 | Barnes |
| 2012/0078218 A1 | 3/2012 | Barnes |
| 2012/0084303 A1 | 4/2012 | Ledford |
| 2012/0116796 A1 | 5/2012 | Bellon |
| 2012/0116800 A1 | 5/2012 | McCallie |

(56) References Cited

U.S. PATENT DOCUMENTS

| | | |
|---|---|---|
| 2012/0123229 A1 | 5/2012 | Butterfield |
| 2012/0124174 A1 | 5/2012 | Nudelman |
| 2012/0130308 A1 | 5/2012 | Silkaitis |
| 2012/0157920 A1 | 6/2012 | Flachbart |
| 2012/0172802 A1 | 7/2012 | Blomquist |
| 2012/0176394 A1 | 7/2012 | Vik |
| 2012/0179093 A1 | 7/2012 | Rinehart |
| 2012/0179136 A1 | 7/2012 | Rinehart |
| 2012/0185267 A1 | 7/2012 | Kamen et al. |
| 2012/0239824 A1 | 9/2012 | Nguyen |
| 2012/0260012 A1 | 10/2012 | Gao-Saari |
| 2012/0302991 A1 | 11/2012 | Blomquist |
| 2012/0310205 A1 | 12/2012 | Lee |
| 2013/0006651 A1 | 1/2013 | Saus |
| 2013/0006666 A1 | 1/2013 | Schneider |
| 2013/0012880 A1 | 1/2013 | Blomquist |
| 2013/0030830 A1 | 1/2013 | Schmoll |
| 2013/0042194 A1 | 2/2013 | Gannon |
| 2013/0045764 A1 | 2/2013 | Vik |
| 2013/0046871 A1 | 2/2013 | Vik |
| 2013/0091191 A1 | 4/2013 | Levin |
| 2013/0104120 A1 | 4/2013 | Arrizza |
| 2013/0133036 A1 | 5/2013 | Wang |
| 2013/0141329 A1 | 6/2013 | Halbert |
| 2013/0177455 A1 | 7/2013 | Kamen et al. |
| 2013/0182381 A1 | 7/2013 | Gray et al. |
| 2013/0184676 A1 | 7/2013 | Kamen et al. |
| 2013/0188040 A1 | 7/2013 | Kamen et al. |
| 2013/0191513 A1 | 7/2013 | Kamen et al. |
| 2013/0197693 A1 | 8/2013 | Kamen et al. |
| 2013/0204188 A1 | 8/2013 | Kamen et al. |
| 2013/0227462 A1 | 8/2013 | Hsu |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo et al. |
| 2016/0158437 A1 | 6/2016 | Biasi et al. |
| 2016/0179086 A1 | 6/2016 | Peret et al. |
| 2016/0184510 A1 | 6/2016 | Kamen et al. |

FOREIGN PATENT DOCUMENTS

| | | | |
|---|---|---|---|
| AU | 2003265858 B2 | 12/2008 | |
| AU | 2003256732 B2 | 7/2009 | |
| EP | 473240 B1 | 6/1994 | |
| EP | 477551 B1 | 1/1995 | |
| EP | 0666699 A1 * | 8/1995 | ............ H04W 16/04 |
| EP | 319268 B1 | 1/1997 | |
| EP | 960627 A2 | 12/1999 | |
| EP | 612004 B2 | 10/2000 | |
| EP | 760244 B1 | 5/2003 | |
| EP | 1640028 A2 | 3/2006 | |
| EP | 1722310 A1 | 11/2006 | |
| EP | 1744262 A2 | 1/2007 | |
| EP | 1944709 A1 | 7/2008 | |
| EP | 2278511 A2 | 1/2011 | |
| EP | 2330524 A2 | 6/2011 | |
| EP | 649316 B2 | 8/2013 | |
| GB | 2020735 A | 11/1979 | |
| JP | 2004523305 A | 8/2004 | |
| JP | 2011124354 A | 6/2011 | |
| WO | WO9304285 A1 | 3/1993 | |
| WO | WO9310835 A1 | 6/1993 | |
| WO | WO9321978 A1 | 11/1993 | |
| WO | WO9814234 A1 | 4/1998 | |
| WO | WO9952575 A1 | 10/1999 | |
| WO | WO 2000/72181 A2 | 11/2000 | |
| WO | WO0198876 A2 | 12/2001 | |
| WO | WO02068018 A2 | 9/2002 | |
| WO | WO02100262 A1 | 12/2002 | |
| WO | WO03094091 A1 | 11/2003 | |
| WO | WO03105931 A1 | 12/2003 | |
| WO | WO2004012043 A2 | 2/2004 | |
| WO | WO2004029853 A2 | 4/2004 | |
| WO | WO2004087241 A1 | 10/2004 | |
| WO | WO2005065750 A1 | 7/2005 | |
| WO | WO2005089263 A2 | 9/2005 | |
| WO | WO2006060291 A2 | 6/2006 | |
| WO | WO2006086723 A2 | 8/2006 | |
| WO | WO2006086735 A2 | 8/2006 | |
| WO | WO2006121510 A2 | 11/2006 | |
| WO | WO2007113709 A1 | 10/2007 | |
| WO | WO2008022880 A1 | 2/2008 | |
| WO | WO2008031821 A1 | 3/2008 | |
| WO | WO2009003196 A1 | 12/2008 | |
| WO | WO2010045119 A2 | 4/2010 | |
| WO | WO2010085867 A1 | 8/2010 | |
| WO | WO 2010/129720 A2 | 11/2010 | |
| WO | WO2011021098 A1 | 2/2011 | |
| WO | WO2011066556 A1 | 6/2011 | |
| WO | WO2011091998 A1 | 8/2011 | |
| WO | WO 2011/119810 A1 | 9/2011 | |
| WO | WO2011109500 A1 | 9/2011 | |
| WO | WO 2013/095459 | 6/2013 | |
| WO | WO/2013/096713 | 6/2013 | |
| WO | WO/2013/096718 | 6/2013 | |
| WO | WO/2013/096722 | 6/2013 | |
| WO | WO/2013/096909 | 6/2013 | |
| WO | WO2013176770 A2 | 11/2013 | |
| WO | WO2013177357 A1 | 11/2013 | |
| WO | WO2014100557 A2 | 6/2014 | |
| WO | WO2014100571 A2 | 6/2014 | |
| WO | WO2014100658 A1 | 6/2014 | |
| WO | WO2014100687 A2 | 6/2014 | |
| WO | WO2014100736 A2 | 6/2014 | |
| WO | WO2014100744 A2 | 6/2014 | |
| WO | WO2014144557 A2 | 9/2014 | |
| WO | WO2015017275 A1 | 2/2015 | |

OTHER PUBLICATIONS

Office Action and Formal Examination dated Aug. 24, 2015, received in Columbian application No. 15168128.
Office Action and Formal Examination dated Aug. 28, 2015, received in Columbian application No. 15167289.
Office Action and Formal Examination dated Sep. 2, 2015, received in Columbian application No. 15168109.
Bianco et al., Architecting Service-Oriented Systems, CMU/SDI-2011-TN-008, Aug. 2011, 46 pages, Software Engineer Institute, Carnegie Mellon University, Hanscom AFB, Massachusetts.
B. Braun, B. Braun SpaceStation MRI, Automated Infusion System, brochure, 1 pg., B. Braun Meslungen AG.

(56) References Cited

OTHER PUBLICATIONS

B. Braun, Dialog+: Dialog with the future, brochure, Oct. 2008, 1-14, Edition Oct. 2008, B. Braun Avitum AG.
B. Braun, Integrated Glucose Control, brochure, 1-11, B. Braun Melsungen AG.
B. Braun, Outlook ES Safety Infusion System, 2008, 16 pgs., B. Braun Medical, Inc.
B. Braun, Perfusor Space PCA and Accessories: Instructions for Use, manual, Nov. 2010, 1-46, B. Braun Melsungen AG.
B. Braun, Space System Technical Data, brochure, , 7 pgs., B. Braun Meslungen AG.
B. Braun, SpaceControl for Automated Glucose Control: Instructions for use, manual, Dec. 2010, 1-43, B. Braun Melsungen AG.
B. Braun, SpaceStation and SpaceCom: Instructions for Use, manual, 1-39, B. Braun Melsungen AG.
B. Braun, The Whole Hospital in the Palm of Your Hand, Automated Infusion Systems, brochure, 1-24, B. Braun Melsungen AG.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety: vol. 2—Observing Medication Administration, 349-364.
Cardinal Health, Alaris DS Docking Station: Technical Service Manual, manual, 2007, 1-31, Issue 2, Cardinal Health, Inc.
Cardinal Health, Alaris Gateway Workstation: Technical Service Manual, manual, 2008, 1-67, Issue 4, Cardinal Health, Inc.
Cardinal Health, Alaris GP Volumetric Pump: Technical Service Manual, manual, 2008, 1-84, Issue 3, Cardinal Health, Inc.
Care Everywhere, Gateway User Manual: V1.0.13 W/CQI 1.6: For use with the Sigma Spectrum Pump: Care Everywhere Document No. CE-100-003-IFU, manual, 1-55, CareEverywhere LLC, 9 Tech Circle, Natick, MA, USA.
Carefusion, Alaris SE Pump: Models 7100/7130 and 7200/7230, Rev2.X—User Manual, manual, Apr. 2011, pp. i-126, CareFusion Corporation, San Diego, CA, United States.
Carefusion, Alaris System Direction for Use—with Alaris PC unit, Model 8015, Dec. 2011, 1-360, CareFusion Corporation, San Diego, CA, United States.
Carefusion, Enhance your skills, methodology and safety performance: Guardrails CQI Reporter Software, 2010, 1-2.
Carefusion, Infusion Products, catalog, 2011, 1-16, CareFusion Corporation, San Diego, CA, United States.
Charter Kontron, Envoy: The Standard for Bedside Patient Monitoring, catalog, England.
Communication pursuant to Article 94(3) EPC dated May 27, 2015, from the European Patent Office for application 11 820 830.5, 1-4.
Communication of the Substantive Examination Result dated Oct. 29, 2015, from the Mexican Institute of Industrial Property for application MX/a/2014/014267, 1-3.
Corsaro et al., Quality of Service in Publish/Subscribe Middleware, Apr. 26, 2006, 1-22, SELEX-SI—Roma.
First Examination Report from The Intellectual Property Office of New Zealand for Application 626636, dated Nov. 13, 2014, 2 pgs.
Food and Drug Administration, Envoy Patient Monitor—Device Modification: Special 510(k) for 12 Lead ECG/Resp. Module, Aug. 16, 2001, 1-12.
Further Examination Report from The Intellectual Property Office of New Zealand for Application 626636, dated Sep. 24, 2015, 2 pgs.
GE Fanuc, Controller Solutions: More Choices for Your Applications, GE Fanuc Controller Solutions catalog, 2004, 1-160, GE Fanuc Automation, Inc.
GE Medical Systems Information Technologies, 510(k) Summary, Aug. 28, 2009, 1-6.
Gieras, Innovative Infusion Pump Technologies, Engineering in Medicine & Biology Society, Jun. 15, 2010, pp. 1-53, IEEE Long Island Chapter.
Goldman et al., Advancing the Adoption of Medical Device "Plug-and-Play" Interoperability to Improve Patient Safety and Healthcare Efficiency, a white paper from the MD PnP Program, Sep. 2009, 1-3, , MD PnP Program.

Goldman et al., Medical Device "Plug-and-Play" Interoperability Program, 2012, MD PnP Program.
Goldman, ASTM final F-2761, Medical Devices and Medical Systems—Essential safety requirements for equipment comprising the patient-centric integrated clinical environment (ICE)—Part 1: General requirements and conceptual model, 2008, 1-34, ASTM.
Goldman, Gaps in the System: Medical Device Interoperability, NIST, Oct. 18, 2006, 1-46, MD PnP.
Hawk, III, The Role of Color Coding in Medication Error Reduction, Action of the AMA House of Delegates 2004 Annual Meeting: Report of the Council on Scientific Affairs, CSA Report 5-A-04, pp. 1-8.
Hewlett Packard, HP Viridia Model 24/26 Series Anesthesia / Standard: Quick Guide, manual, 1998, 1-29, Hewlett Packard.
Hoenich et al., Research & Technology: The Current Status and Future Directions of Hemodialysis Machine Technology, Hemodialysis Horizons, 38-44, AAMI.
Infusion Nurses Society, Infusion Nursing Standards of Practice, Journal of Infusion Nursing, Jan./Feb. 2011, pp. S1-S110, vol. 34, No. 1S, Infusion Nurses Society.
Infusion Nurses Society, Policies and Procedures for Infusion Nursing, 2011, 1-162, 4th edition, Infusion Nurses Society, Inc.
International Search Report & Written Opinion dated Aug. 7, 2014, received in International patent application No. PCT/US2013/076851, 19 pgs.
International Search Report & Written Opinion dated Sep. 4, 2014, received in International patent application No. PCT/US2013/077258, 18 pgs.
International Search Report & Written Opinion dated Jul. 14, 2014, received in International patent application No. PCT/US2013/077135, 18 pgs.
International Preliminary Report on Patentability dated Jul. 3, 2014, received in International patent application PCT/US2011/066588, 6 pgs.
International Preliminary Report on Patentability dated Jul. 2, 2015, received in International patent application No. PCT/US2013/076851, 13 pgs.
International Preliminary Report on Patentability dated Jul. 2, 2015, received in International patent application No. PCT/US2013/077258, 13 pgs.
International Preliminary Report on Patentability dated Dec. 4, 2014, received in International patent application No. PCT/US2013/042350, 13 pgs.
International Preliminary Report on Patentability dated Jul. 2, 2015, received in International patent application No. PCT/US2013/077135, 13 pgs.
ISO/IEC, Information Technology—Open Systems Interconnection—Basic Reference Model: The Basic Model, Nov. 15, 1994, 1-59, Second edition (Corrected and reprinted Jun. 15, 1996), ISO/IEC, Geneva, Switzerland.
Israelski, The Symbiq (Next-Generation) IV Infusion Pump: A Feature-Filled "Intelligent" Pump Developed with and for the End-User, May 2007, 1-4, Hospira, Inc.
Invitation to Pay Additional Fees and, Where Applicable, Protest Fee dated May 6, 2014, received in International patent application No. PCT/US2013/077135, 6 pgs.
Joshi et al., OMG's Data Distribution Service Standard: The OMG Data Distribution Service (DDS) Standard specifies a mandatory API for data-centric publish-subscribe, Dr. Dobb's: The World of Software Development, Nov. 20, 2006, 1-9.
Millard et al., XEP-0060: Publish-Subscribe, Jul. 12, 2010, 1-173, Version 1.13, XMPP Standards Foundation (XSF).
National Patient Safety Agency, Design for Patient Safety: A Guide to the Design of Electronic Infusion Devices, booklet, 2010, pp. 1-96, Edition 1, National Patient Safety Agency, London, USA.
Nemeth et al., Making Information Technology a Team Player in Safety: The Case of Infusion Devices, Advances in Patient Safety: Interface Design for Infusion Devices, pp. 319-330, vol. 1, Feb. 2005.
Notice for Reason for Rejection, dated Oct. 6, 2015, received in Japanese patent application National Publication No. 2014-548986, 5 pgs.

(56) References Cited

OTHER PUBLICATIONS

Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.
Prusch et al., IV Interoperability: Smart Pump and BCMA Integration, brochure, Oct. 5, 2010, 1-13, Lancaster General Health.
Rafferty, Proposal for Wireless Transmission of Non-invasive Respiratory Data to the Servo Module of an Opioid Infusion-Pump for Real-Time Patient Safety Feedback Control, Yale School of Medicine (Publication date unknown but assumed to be prior to the filing date).
Search Report and Written Opinion from The Intellectual Property Office of Singapore for Application 11201403511Y, dated Feb. 9, 2015, 22 pgs.
Sprunk et al., System Design for Simultaneous Data Acquisition from Patient Monitor and Syringe Pumps in Intensive Care Unit, Dec. 17-19, 2010, 878-882, IEEE EMBS International Conference on Biomedical Engineering and Sciences, Langkawi.
Talbot et al., Making Stretchable Electronics, Technology Review, Aug. 21, 2012,Sep./Oct. 1-2, 2012, MIT.
The 2008 Annual Premier Breakthroughs Conference: Innovation Through Supply Chain, Technology, and Clinical Sessions, Christine Depietto, Supply Synergy, vol. 3, No. 2, Aug. 2008.
Turisco et al., Beyond E-Health Records, CSC World, Winter 2010, 26-29, CSC World.
Turisco et al., Equipped for Efficiency: Improved Nursing Care Through Technology, Dec. 2008, 1-29, California HealthCare Foundation.
Vanderveen, Technology Focus: Using Data to Improve Smart Intravenous Infusion Pumps, Human Factors Horizons, 2010, pp. 57-63, Human Factors Horizons.
Definition—wifi as downloaded on Jul. 23, 2015, 1 pg.
Wikipedia, Publish-Subscribe Pattern, Jul. 31, 2013, 1-5.
Wikipedia, RSS definition, as downloaded on Jul. 21, 2015, p. 1-9.
Written Opinion from The Intellectual Property Office of Singapore for Application 11201403511Y, dated Jun. 19, 2015, 11 pgs.
Written Opinion from The Intellectual Property Office of Singapore for Application 11201403511Y, dated Oct. 13, 2015, 11 pgs.
Invitation to Pay Additional Fees and, Where Applicable, Protest Fee dated Sep. 26, 2013, received in International patent application No. PCT/US2013/042350, 7 pgs.
International Search Report & Written Opinion dated Nov. 7, 2013, received in International patent application No. PCT/US2013/042350, 18 pgs.
Gregorczyk, David, et al., "A Proof of Concept for Medical Device Integration Using Web Services," 9th Annual International Multi-Conference on Systems, Signals and Devices, Mar. 20-23, 2012, 6pgs.
Mauro, Christina, et al., "Standardized Device Services—A Design Pattern for Services Oriented Integration of Medical Devices" Proceedings of the 43rd Hawaii International Conference on System Sciences , Jan. 5-8, 2010, 10 pgs.
Trinugroho, Yohanes Baptista Dafferianto, et al. "A SOA-Based eHealth Service Platform in Smart Home Enviroment" 13th International Conference on e-Health Networking, Applications and Services: Healthcom 2011 :Jun. 13-15, 2011, Columbia, Missouri, USA, 4 pgs.
Invitation to Pay Additional Fees and, Where Applicable, Protest Fee dated May 19, 2014, received in International patent application No. PCT/US2013/077258, 7 pgs.
Invitation to Pay Additional Fees and, Where Applicable, Protest Fee dated May 23, 2014, received in International patent application No. PCT/US2013/076851, 8 pgs.
U.S. Appl. No. 61/860,398, filed Jul. 31, 2013.
U.S. Appl. No. 61/894,801, filed Oct. 23, 2013.
U.S. Appl. No. 29/471,856, filed Nov. 6, 2013, USD0751689S.
U.S. Appl. No. 29/471,864, filed Nov. 6, 2013, USD0752209S.
U.S. Appl. No. 29/471,861, filed Nov. 6, 2013, USD0749206S.
U.S. Appl. No. 29/471,859, filed Nov. 6, 2013, USD0745661S.
U.S. Appl. No. 29/471,858, filed Nov. 6, 2013, USD0751690S.
U.S. Appl. No. 61/900,431, filed Nov. 6, 2013.
U.S. Appl. No. 61/904,123, filed Nov. 14, 2013.
U.S. Appl. No. 14/101,848, filed Dec. 10, 2013, US20140165703A1.
U.S. Appl. No. 29/477,249, filed Dec. 20, 2013.
PCT/US13/77270, filed Dec. 20, 2013, WO/2014/100744A1.
U.S. Appl. No. 29/477,233, filed Dec. 20, 2013.
U.S. Appl. No. 29/477,236, filed Dec. 20, 2013.
U.S. Appl. No. 29/477,242, filed Dec. 20, 2013, USD0756386S.
U.S. Appl. No. 29/477,237, filed Dec. 20, 2013.
U.S. Appl. No. 29/477,231, filed Dec. 20, 2013.
PCT/US13/77135, filed Dec. 20, 2013, WO/2014/100687A1.
U.S. Appl. No. 14/136,243, filed Dec. 20, 2013, US20140188516A1.
U.S. Appl. No. 29/477,232, filed Dec. 20, 2013.
U.S. Appl. No. 14/137,562, filed Dec. 20, 2013, US20140227021A1.
PCT/US13/77077, filed Dec. 20, 2013, WO/2014/100658A1.
U.S. Appl. No. 14/135,784, filed Dec. 20, 2013, US20140188076A1.
U.S. Appl. No. 14/135,809, filed Dec. 20, 2013, US20140195639A1.
PCT/US13/76851, filed Dec. 20, 2013, WO2014100557A1.
U.S. Appl. No. 14/137,421, filed Dec. 20, 2013, US20140180711A1.
PCT/US13/77258, filed Dec. 20, 2013, WO2014100736A1.
PCT/US13/76886, filed Dec. 20, 2013, WO/2014/100571A1.
U.S. Appl. No. 61/942,986, filed Feb. 21, 2014.
U.S. Appl. No. 14/191,827, filed Feb. 27, 2014, US20150238228A1.
PCT/US14/29020, filed Mar. 14, 2014, WO/2014/144557A1.
U.S. Appl. No. 61/953,036, filed Mar. 14, 2014.
U.S. Appl. No. 14/213,373, filed Mar. 14, 2014, US20140318639A1.
U.S. Appl. No. 61/987,742, filed May 2, 2014.
U.S. Appl. No. 61/990,330, filed May 8, 2014.
U.S. Appl. No. 14/341,207, filed Jul. 25, 2014, US20150033823A1.
PCT/US2014/48227, filed Jul. 25, 2014, WO2015017275A1.
U.S. Appl. No. 14/451,904, filed Aug. 5, 2014, US20140343492A1.
U.S. Appl. No. 61/052,008, filed Sep. 18, 2014.
U.S. Appl. No. 14491,143, filed Sep. 19, 2014, US20150002668A1.
U.S. Appl. No. 14/491,128, filed Sep. 19, 2014, US20150002667A1.
U.S. Appl. No. 14/491,161, filed Sep. 19, 2014, US20150002677A1.
U.S. Appl. No. 62/086,356, filed Dec. 2, 2014.
U.S. Appl. No. 14/616,079, filed Feb. 6, 2015, US20150154364A1.
U.S. Appl. No. 29/517,097, filed Feb. 10, 2015.
U.S. Appl. No. 29/517,101, filed Feb. 10, 2015.
U.S. Appl. No. 29/517,100, filed Feb. 10, 2015.
U.S. Appl. No. 29/517,098, filed Feb. 10, 2015, USD0754065S.
U.S. Appl. No. 29/517,096, filed Feb. 10, 2015.
U.S. Appl. No. 29/517,095, filed Feb. 10, 2015.
U.S. Appl. No. 29/517,099, filed Feb. 10, 2015.
U.S. Appl. No. 14/627,287, filed Feb. 20, 2015, US20150157791A1.
PCT/US15/16796, filed Feb. 27, 2015.
U.S. Appl. No. 14/656,945, filed Mar. 13, 2015, US20150257974A1.
U.S. Appl. No. 14/679,364, filed Apr. 6, 2015, US20150314083A1.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 14/812,149, filed Jul. 29, 2015, US20150332009A1.
U.S. Appl. No. 29/538,153, filed Sep. 1, 2015.
U.S. Appl. No. 62/212,871, filed Sep. 1, 2015.
PCT/US15/49952, filed Sep. 14, 2015.
U.S. Appl. No. 14/853,300, filed Sep. 14, 2015, US20160158437A1.
U.S. Appl. No. 14/873,515, filed Oct. 2, 2015, US20160097382A1.
U.S. Appl. No. 14/931,928, filed Nov. 4, 2015, US20160055397A1.
U.S. Appl. No. 14/932,291, filed Nov. 4, 2015, US20160055649A1.
U.S. Appl. No. 14/938,083, filed Nov. 11, 2015, US20160073063A1.
U.S. Appl. No. 14/938,368, filed Nov. 11, 2015, US20160061641A1.
U.S. Appl. No. 14/939,586, filed Nov. 12, 2015, US20160131272A1.
U.S. Appl. No. 14/939,015, filed Nov. 12, 2015, US20160063353A1.
PCT/US2015/63359, filed Dec. 2, 2015.
U.S. Appl. No. 14/956,648, filed Dec. 2, 2015, US20160084434A1.
U.S. Appl. No. 29/547,402, filed Dec. 3, 2015.
U.S. Appl. No. 29/547,405, filed Dec. 3, 2015.
U.S. Appl. No. 29/548,225, filed Dec. 11, 2015.
U.S. Appl. No. 29/552,303, filed Jan. 21, 2016.
U.S. Appl. No. 29/552,943, filed Jan. 27, 2016.
U.S. Appl. No. 29/552,942, filed Jan. 27, 2016.
U.S. Appl. No. 62/288,132, filed Jan. 28, 2016.

(56) References Cited

OTHER PUBLICATIONS

U.S. Appl. No. 29/553,094, filed Jan. 28, 2016.
U.S. Appl. No. 29/556,048, filed Feb. 26, 2016.
U.S. Appl. No. 15/055,941, filed Feb. 29, 2016, US20160179086A1.
U.S. Appl. No. 15/059,394, filed Mar. 3, 2016, US20160184510A1.
U.S. Appl. No. 15/077,389, filed Mar. 22, 2016.
U.S. Appl. No. 29/561,572, filed Apr. 18, 2016.
U.S. Appl. No. 29/564,750, filed May 16, 2016.
U.S. Appl. No. 15/161,876, filed May 23, 2016.
U.S. Appl. No. 62/341,396, filed May 25, 2016.
U.S. Appl. No. 29/565,908, filed May 25, 2016.
U.S. Appl. No. 15/163,906, filed May 25, 2016.
U.S. Appl. No. 29/569,460, filed Jun. 28, 2016.
U.S. Appl. No. 29/569,450, filed Jun. 28, 2016.
U.S. Appl. No. 15/205,538, filed Jul. 8, 2016.
U.S. Appl. No. 29/570,648, filed Jul. 11, 2016.
U.S. Appl. No. 29/571,387, filed Jul. 18, 2016.
U.S. Appl. No. 13/011,543, filed Jan. 21, 2011.
U.S. Appl. No. 13/011,543, B1-B56, C1-C81.
International Search Report & Written Opinion dated May 14, 2012, received in International patent application No. PCT/US2011/066588, 9 pgs.
Office Action dated May 22, 2012, received in U.S. Appl. No. 13/011,543, 7 pgs.
Office Action dated Jun. 10, 2013, received in U.S. Appl. No. 13/011,543, 15 pgs.
Hofmann, "*Modeling Medical Devices for Plug-and-Play Interoperability*", Master of Engineering Thesis, Massachusetts Institute of Technology, Jun. 2007, © Robert Matthew Hofmann, MMVII, pp. 1-187.
King et al., "*Prototyping Closed Loop Physiologic Control with the Medical Device Coordination Framework*", University of Pennsylvania, Kansas State University, © 200X ACM X-XXXXX-XX-X/XX/XX, pp. 1-11.
Jetley et al., *Safety Requirements Based Analysis of Infusion Pump Software*, Office of Science and Engineering Laboratories, Center for Devices and Radiological Health, US Food and Drug Administration, Silver Spring, MD 20993-0002, pp. 1-4.
FDA US Food and Drug Administration, "*SEDASYS® Computer-Assisted Personalized Sedation System—P080000*", Jul. 16, 2013, pp. 1-2, www.fda.gov/MedicalDevices/ProductsandMedicalProcedures/DeviceApprovalsandClearances/Recently-ApprovedDevices/ucm353950.htm.
U.S. Appl. No. 61/297,544, filed Jan. 22, 2010.
U.S. Appl. No. 13/333,574, filed Dec. 21, 2011.
PCT/US11/66588, filed Dec. 21, 2011.
U.S. Appl. No. 61/578,649, filed Dec. 21, 2011.
U.S. Appl. No. 61/578,658, filed Dec. 21, 2011.
U.S. Appl. No. 61/578,674, filed Dec. 21, 2011.
U.S. Appl. No. 61/679,117, filed Aug. 3, 2012.
U.S. Appl. No. 61/651,322, filed May 24, 2012.
U.S. Appl. No. 61/738,447, filed Dec. 18, 2012.
U.S. Appl. No. 13/723,238, filed Dec. 21, 2012.
U.S. Appl. No. 13/723,235, filed Dec. 21, 2012.
PCT/US12/71131, filed Dec. 21, 2012.
U.S. Appl. No. 13/724,568, filed Dec. 21, 2012.
U.S. Appl. No. 13/725,790, filed Dec. 21, 2012.
PCT/US12/71490, filed Dec. 21, 2012.
U.S. Appl. No. 13/723,239, filed Dec. 21, 2012.
U.S. Appl. No. 13/723,242, filed Dec. 21, 2012.
U.S. Appl. No. 13/723,244, filed Dec. 21, 2012.
PCT/US12/71142, filed Dec. 21, 2012.
U.S. Appl. No. 61/740,474, filed Dec. 21, 2012.
U.S. Appl. No. 13/723,251, filed Dec. 21, 2012.
PCT/US12/71112, filed Dec. 21, 2012.
U.S. Appl. No. 13/723,253, filed Dec. 21, 2012.
U.S. Appl. No. 13/840,339, filed Mar. 15, 2013.
PCT/US13/32445, filed Mar. 15, 2013.
U.S. Appl. No. 13/833,432, filed Mar. 15, 2013.
U.S. Appl. No. 13/836,497, filed Mar. 15, 2013.
U.S. Appl. No. 13/833,712, filed Mar. 15, 2013.
U.S. Appl. No. 29/457,516, filed Jun. 11, 2013.
U.S. Appl. No. 29/457,520, filed Jun. 11, 2013.
U.S. Appl. No. 29/457,521, filed Jun. 11, 2013.
U.S. Appl. No. 29/457,522, filed Jun. 11, 2013.
U.S. Appl. No. 13/834,030, filed Mar. 15, 2013.
U.S. Appl. No. 13/900,655, filed May 23, 2013.
PCT/US13/42350, filed May 23, 2013.
U.S. Appl. No. 61/843,574, filed Jul. 8, 2013.
U.S. Appl. No. 13/011,543, B1-B8, C1 and C4-C7.

\* cited by examiner

ELECTRONIC PATIENT MONITORING SYSTEM

CROSS-REFERENCES

The present application is a continuation of U.S. non-provisional application Ser. No. 13/011,543 filed on Jan. 21, 2011, still and entitled Electronic patient Monitoring System, which claims the benefit of prior U.S. provisional application No. 61/297,544 filed on Jan. 22, 2010 and entitled Electronic Order Intermediation System for a Medical Facility. Each of these applications is hereby incorporated by reference herein in its entirety.

BACKGROUND

The present invention relates to systems and methods to provide electronic intermediation among medical devices delivering treatments to patients, medical devices monitoring parameters associated with those patients, and health care providers who order, process or initiate those treatments. An object of the invention is to reduce the incidence of medical treatment errors, and to improve the efficiency of tracking a patient's course of treatment.

Despite the existence of systems incorporating electronic medical records ("EMR"), and computerized provider order entry ("CPOE"), the process of ordering and delivering medical treatments still has the potential to cause critical information to be miscommunicated, to allow treatment decisions to be made without ready access to complete information, and to delay implementation of treatment orders due to unnecessarily redundant and inefficient procedures. An approach to dealing with this problem is illustrated herein by using medication ordering as an example. It should be noted, however, that the invention as described herein can be applied to other treatment or diagnostic decisions involving the care of a patient.

Medication errors may be responsible for over 300 deaths and may injure over one million people each year in the United States. Hospitals under financial stress may experience an increased incidence of medication errors. Medications associated with the most dangerous errors include insulin, narcotics, heparin and chemotherapy. Sources of error include administering the wrong drug, the wrong concentration of drug, at the wrong rate, or via the wrong route (medications can be administered orally, intravenously, intramuscularly, subcutaneously, rectally, topically to the skin, eye or ear, intrathecally, intraperitoneally or even intravesically). Even with proper orders and proper labeling, medications still can be administered improperly because of illegible handwriting, miscommunication of orders, and mispronunciation of drugs having similar names. The trend toward the use of electronic medical records (EMR), and bar coding systems for medications has been shown to reduce the incidence of medication errors. EMR systems, for example, can facilitate computerized provider order entry (CPOE), and flag orders for drugs that do not match a patient's characteristics such as diagnosis, allergies, weight or age. However, these systems have not been widely adopted, and their implementation can result in significant delays and inefficiencies in ordering, preparing and administering medications.

It has been estimated that medication infusion devices are involved in up to one third of all medication errors that result in significant harm. The wrong drug may be hung, incorrect parameters (e.g. drug concentration or rate of infusion) may be entered, or existing infusion parameters may be improperly changed. Of infusion pump-related deaths, nearly half may be due to user error, and most of these may be due to errors in programming the infusion device.

An effective Monitoring system should monitor and intercede at any phase of the medication ordering and administration process to help minimize any of a number of adverse events that could result from the treatment. The medication treatment process conceptually can be separated into three phases: a prescription phase, a medication preparation phase, and an administration phase. Errors can occur when a prescription is written or entered, when a drug is retrieved for use or mixed in solution, or when it is administered to the patient. It would be particularly desirable for a monitoring system to not significantly impair the efficiency with which medications are ordered, prepared or administered, and preferably to actually reduce the time required to perform those activities by collecting, organizing and presenting relevant real-time information to the user.

SUMMARY

In an exemplary embodiment involving the ordering and administration of medications, the Electronic Patient Monitoring system may comprise a first data-gathering module (e.g., a Monitoring Client) and a second order-input module (e.g. a fixed or portable communications device) having a user interface for transmitting an order or receiving patient-related information. The first module may be configured to receive and store measured parameters pertaining to a patient's current condition, such as blood pressure, heart rate, heart rhythm, temperature, oxygenation, respiratory rate, or ventilation, for example. The first module may also be configured to receive information about pre-existing parameters related to the patient from a first database (e.g. an EHR database containing information about the patient), including drug allergies or sensitivities, other currently administered drugs, age, weight, height, kidney or liver function, for example. The first module may also be configured to obtain medication information about the ordered medication and/or pre-existing drugs from a second database (e.g. a drug information database), such as known drug interactions, effects of the medication or pre-existing drugs on blood pressure, pulse, heart rhythm, or respirations, for example. The first module can be configured to compare the patient's currently measured parameters and received pre-existing parameters with known normal ranges, and create a table of patient parameters found to be outside the normal ranges. The first module may then compare the table of patient parameters with a table of corresponding parameters obtained from the drug information database. If a match is found to exist between the table of patient parameters and the table of corresponding parameters, the first module may then retrieve one or more pre-entered and stored messages for transmission to the second (order input) module. These messages may include, for example, warnings to a user of the second module that are appropriate for the particular medication ordered, the patient's pre-existing drugs, and the patient's current and pre-existing medical condition. Optionally, further repetitions of warnings may be avoided once a warning has been received by the second module, and the warning has been acknowledged by the user of the second module through an input signal from the user interface.

In other embodiments, the Electronic Patient Monitoring system may provide the user with editable default values derived from standard dosing and administration guidelines obtained from the drug information database, and can alert the user to modifications that may be indicated based on the patient's current and pre-existing medical condition, allergies or other existing drugs. The Monitoring system preferably minimizes the amount of typed input required of a user.

In other embodiments, the first module or other modules of the Electronic Patient Monitoring system may also be used to identify ordered medications to be delivered to the patient's bedside (through the use of, for example, bar codes and readers or RFID tags and scanners), and verify that the appropriate medication and dosage are being prepared and delivered to the patient. In an embodiment, the first module may also interact either in a hard-wired or wireless fashion with a device that administers treatment, such as a solution/medication infusion pump. In the case of an infusion pump, the first module or another connected module may provide the pump with infusion settings such as flow rate or infusion pressure, and receive from it various state parameters such as, for example, the presence of air in the infusion line, the amount of solution remaining in an IV bag to which it is connected, or the pressure of fluid in the infusion line. If the parameters are found to be abnormal, the first module may be configured to respond by signaling the pump to halt infusion, alter the rate of infusion, and/or alert a health care provider or others of the abnormality, either directly through an alarm incorporated in the first module, or by transmission of an alarm to the second module. In a further embodiment, the first module may also be configured to communicate with various medical devices used to monitor a patient's condition, such as, for example, blood pressure monitors, ECG monitors, pulse oximetry monitors, temperature monitors, and the like. In some cases, the first module can be programmed to emit an alert to the patient or other persons if the monitored parameters fall outside a pre-determined range. In some embodiments, the first module can transmit a signal to a monitoring device to conduct an unscheduled measurement by the device. The first module may communicate with various health care providers at various locations, and in an embodiment may be able to notify the patient to whom it is assigned of an abnormality, and recommend corrective action through, for example an audible alert or recorded message.

DETAILED DESCRIPTION

Figure 1:
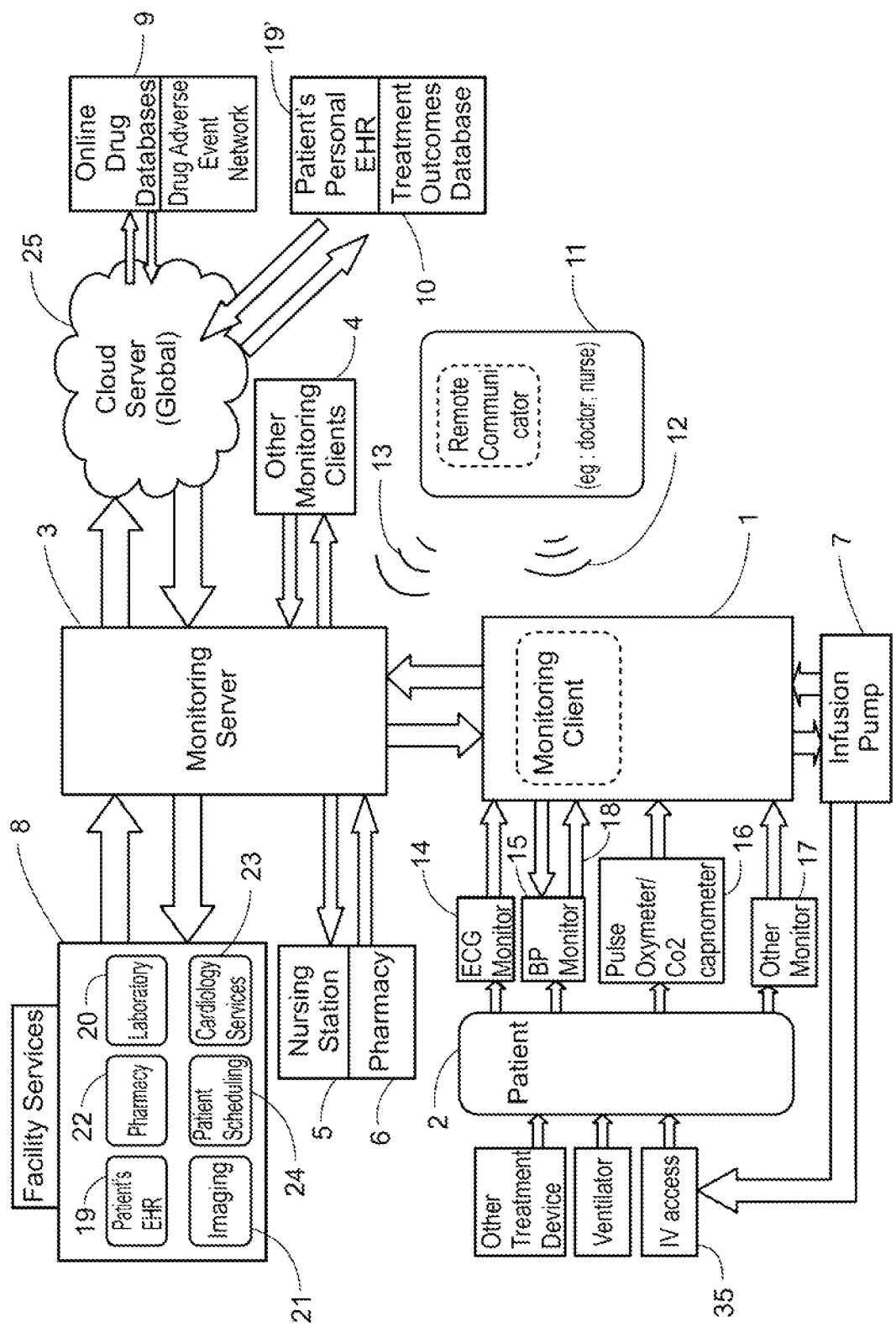
FIG. 1 is a schematic representation of an exemplary Electronic Patient Monitoring system, showing paths of communication among system components.

As shown in FIG. 1, components of the Electronic Patient Monitoring System may include one or more Monitoring Clients 1,4, each of which may be assigned and in physical proximity to an individual patient 2, and a more remote Monitoring Server 3 for the uploading of information from a number of Monitoring Clients 1,4, and for downloading information and instructions from various sources to the Monitoring Clients 1,4. When in the patient's room, a health care provider can interact directly with a Monitoring Client 1 to obtain information about the patient 2 or to enter orders pertaining to the patient 2. Alternatively, providers at remote locations (e.g., doctor's office, nursing station 5, hospital pharmacy 6) may interact with an individual Monitoring Client 1 through a communications link with the Monitoring Server 3, or directly via a hospital local area network having each Monitoring Client 1,4 as a node.

In an embodiment, each Monitoring Client 1 is assigned to a specific patient 2, and can be a desk-based, portable or hand-held controller with display and user input capability. Preferably, it is portable and allows for efficient data viewing and data entry, such as a notebook PC, netbook PC, tablet PC, or even a 'smart-phone,' with or without touch screen capability. The designation of a particular Monitoring Client 1 to a particular patient 2 may be made using any of a number of methods, including (but not limited to) a unique patient identifier using a bar coded or RFID tag-embedded wrist band, for example. The Monitoring Client 1 may include one or more microprocessors to send and receive information relevant to the patient's care or condition. In some embodiments, the Monitoring Client 1 may be physically associated with a medical infusion pump 7 either permanently or detachably. This can be accomplished by a docking interface between the two devices. The Monitoring Client 1 can communicate with the pump 7 in a number of ways, including, for example, through electrical contacts in the docking interface, by means of an electrical connector, or wirelessly by means of transceivers on each device. The Monitoring Client 1 can also communicate with other databases in the facility 8, with databases external to the facility 9,10, and with health care providers via portable communications devices 11 (including, for example, physicians, nurses, and pharmacists). This can be accomplished by a wired connection to a facility server through a connector in the patient's room (such as, for example, a Category 5 local area network connector), or wirelessly 12. In one embodiment, access to intra and extra facility databases is mediated 13 through the Monitoring Server 3, which can then centralize the software and application programming interfaces required to communicate with databases having disparate organization, formatting and communications protocols. Thus, in an embodiment, any software updates may be largely limited to the Monitoring Server 3, reducing the maintenance requirements on the individual Monitoring Clients 1,4. Optionally, a Monitoring Client 1 can communicate with medical treatment devices such as infusion pumps 7 to receive information about the progress of treatment, and to provide operational instructions to the treatment device. In another embodiment, the Monitoring Client 1 may also communicate with medical diagnostic or monitoring devices (such as, for example, an electrocardiographic (ECG) monitor 14, a blood pressure (BP) monitor 15, a pulse oximeter or CO2 capnometer 16, or other devices such as temperature monitors, etc.) to receive readout information from the devices, and potentially to instruct 18 the devices to take a reading when desired by a provider or by algorithm.

In an embodiment, the Monitoring Client 1 has the ability to communicate and interact directly with a health care provider using a hand-held or portable communications device 11. This may be conveniently accomplished wirelessly 12, so that communications can be maintained regardless of the patient's location in the facility, or the provider's location either within or outside the facility. In one aspect, information specific to the patient 2 can be stored locally in the Monitoring Client 1, so that the patient's health care provider can access the information directly without having to access the Monitoring Server 3. By incorporating appropriate safety and security clearances, changes to the settings or flow parameters of a connected infusion pump 7 or monitoring device 14-17 can be accomplished directly between a provider's communications device 11 and the Monitoring Client 1, with selected changes being also communicated to Monitoring Server 3, and thence to other appropriate locations, such as the Nursing Station 5, and/or Pharmacy 6. Furthermore, any new order pertaining to the patient 2 may be entered in the ordering provider's communications device 11 and transmitted to the Monitoring Client 1, which in turn can then notify the care giver (e.g. RN) via the care giver's own portable communications device 11. Preferably, any information acquired and stored in the Monitoring Client 1 is periodically uploaded to the Monitoring Server 3 and stored in a patient-specific database. Thus, if a patient's Monitoring Client 1 needs to be taken out of service, a new device can be assigned to the patient 2 and quickly re-populated with the patient's current information from the Monitoring Server 3. Orders, medications, progress notes, monitoring and treatment data from the patient's attached devices may also be uploaded from the Monitoring Client 1 to the patient's EHR 19, 19' for permanent storage.

The Monitoring Server 3 may comprise a computer that can communicate with and provide some elements of control for a number of Monitoring Clients 4 in the facility. It may provide a Monitoring Clients 1, 4 with data extracted from a number of databases both within 8 and outside 9 of the facility. In an embodiment, the Monitoring Server 3 can interrogate the facility's EHR system 19 for targeted information pertaining to a patient 2, and then populate that patient's Monitoring Client 1 with a pre-defined set of information (such as, for example, the patient's age, height, weight, categories of diagnoses, current medications and medication categories, medication allergies and sensitivities, etc.). The Monitoring Server 3 may establish a link to EHR 19, Laboratory 20, Radiology 21, Pharmacy 22 and other systems (such as, e.g., Cardiology 23 or Scheduling database 24) in the facility when, for example, a Monitoring Client 1 has been assigned to a patient 2. With a unique patient identifier, the Monitoring Server 3 can obtain electronic access (permission) to receive and send patient-specific data from and to these systems. A pre-determined (but selectable) subset of the data may be downloadable into the Monitoring Client 1 memory. The information thus acquired can then serve as a key database against which new orders can be analyzed. Orders entered into a Monitoring Client 1 can be checked for compatibility with the patient-specific information obtained by the Monitoring Server 3. Optionally, for safety redundancy, orders entered remotely from a portable communications device 11 can be intercepted by the Monitoring Server 3 and similarly can be checked. The Monitoring Server 3 may also obtain information from medication databases residing in the facility's pharmacy 22 or externally 9 to determine whether a new patient order may generate an incompatibility with a patient's existing medications, for example. In an embodiment, the Monitoring Server 3 may be programmed to access publicly available internet sites 25 to determine whether new information pertaining to the patient's ordered medication should be downloaded and transmitted 13 in an alert to the patient's health care provider(s). The Monitoring Server 3 may also route information between remote portable communications devices 11 and a patient's Monitoring Client 1.

In an embodiment, the patient's physician, nurse or pharmacist may have access to the patient's Monitoring Client 1 to relay or receive new orders (such as medication orders, for example) pertaining to the patient 2. The Monitoring Client 1 or Server 3 may then log the new order and relay the request to the pharmacist 6, and the patient's nurse via the nurse's portable communications device 11 and/or via a fixed terminal at the nursing station 5. A 'smart phone' having a customized communications application with Monitoring Client 1 (such as, e.g., a Google Nexus One phone or Apple i-phone, among others) may serve as a convenient portable communications device 11 for providers who are not at a fixed location (such as at an office or remote nursing station). A tablet PC, netbook, or laptop computer may also serve as a convenient portable communications device 11 for both portable and fixed locations. A PC may act as a convenient communication device 11 for fixed or desktop locations. If a provider is located in the patient's room, he or she may enter or receive information pertaining to the patient 2 using a direct input through a keyboard or touch screen on the Monitoring Client 1.

Example of Monitoring-Assisted Order Entry

Figure 2:
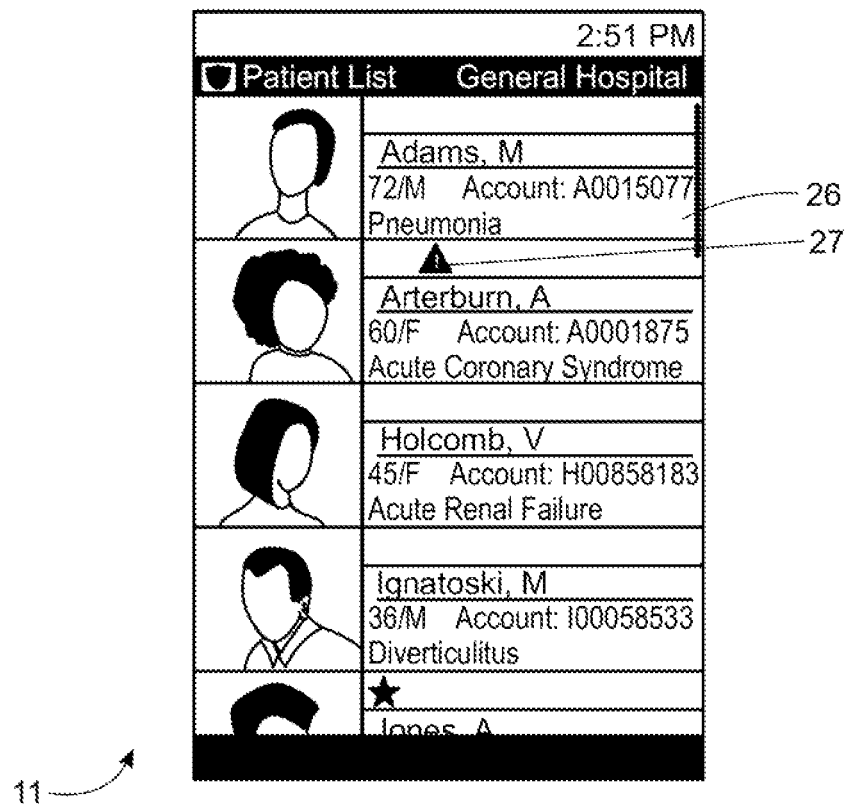
FIG. 2 is an illustration of a display screen on a health care provider's portable communications device, showing a list of patients whose information the provider can access.

The functionality of the Patient Monitoring system can be illustrated by an example in which an ordering provider enters a new medication prescription for a patient. In this scenario, the physician may view his list of admitted patients on his hand-held device after entering the appropriate security pass code. In this example, the physician's patients can be listed as shown in FIG. 2, with limited and user-selectable information 26 on each patient, such as, for example, age, diagnosis, and medical record number. Alert symbols 27 may be transmitted by the Monitoring Client 1 to the physician's device 11 if, for example, orders for the patient 2 are incomplete, the nurse has flagged the patient for attention, or if the Monitoring Client 1 has received input from a database or a patient monitoring device 14-17 that has exceeded a pre-determined threshold for physician notification.

Figure 3:
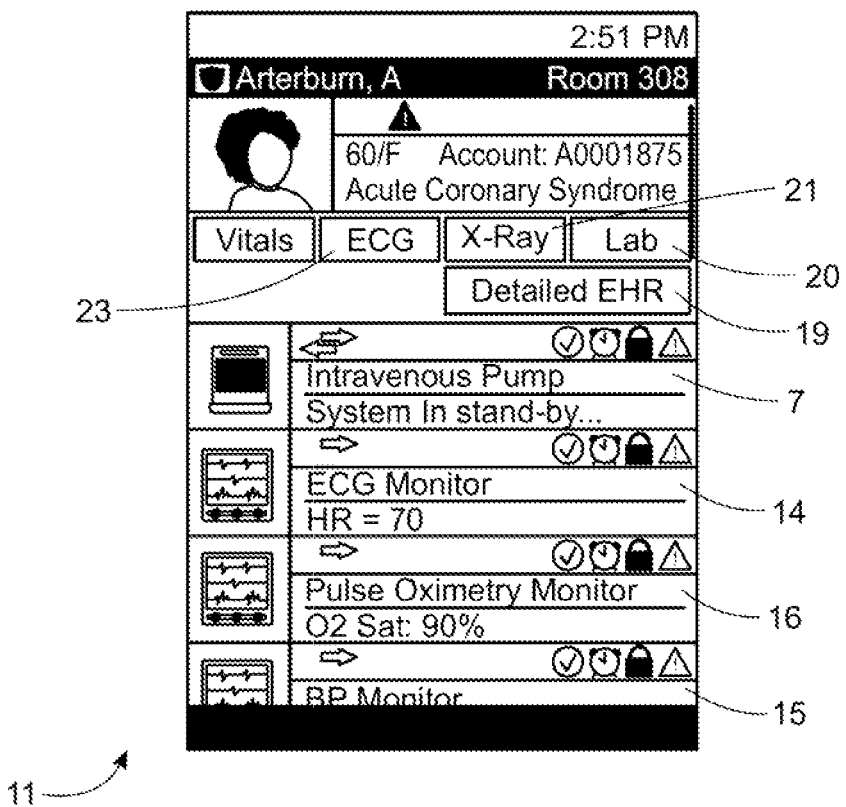
FIG. 3 is an illustration of a display screen on a health care provider's portable communications device, showing devices associated with a particular patient, with current data from the devices and one-touch access to some of the patient's medical information.

After the physician selects a patient for further review, a display such as that shown in FIG. 3 may be transmitted to the physician's device 11. The physician can view user-selectable data originating from monitors 14-17 to which the patient is connected, and the physician may have one-touch access to a number of databases 19-21, 23 containing patient-specific information. In an embodiment, the Monitoring Client 1 may be connected or docked to an infusion pump 7 available for use with the patient 2. In a scenario illustrated in FIG. 3, the physician can press on the icon representing the infusion pump 7 to order an intravenous medication for the patient 2.

Figure 4:
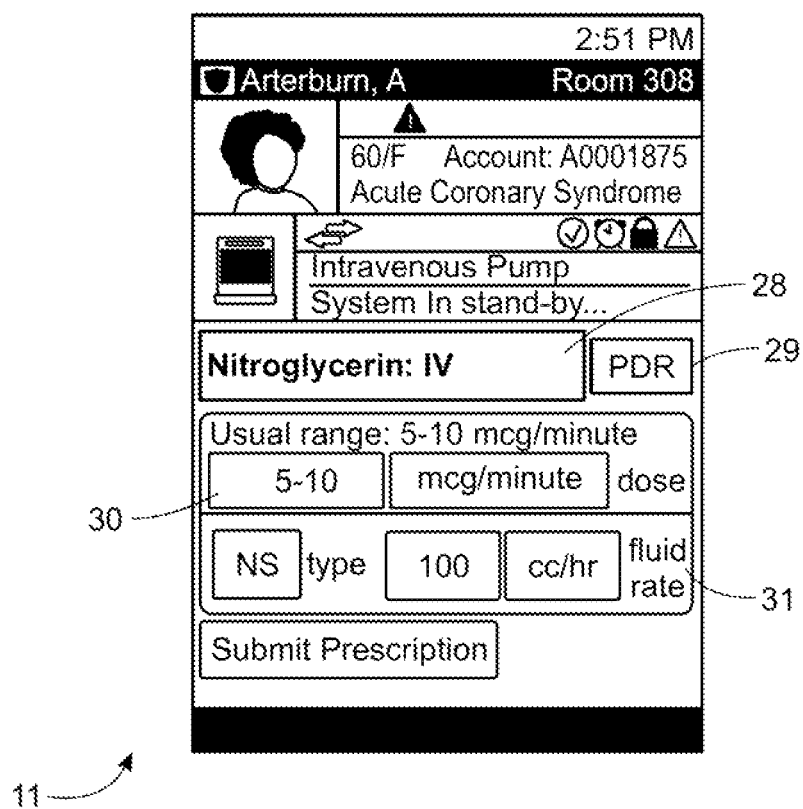
FIG. 4 is an illustration of a display screen on a health care provider's portable communications device, showing data entry fields for a prescription for a medication for use with an intravenous infusion pump.

FIG. 4 shows one of a number of possible prescription ordering screens with which a physician can remotely order a medication. In the example illustrated, the physician enters the drug IV Nitroglycerin 28, which may be entered by typing or via a drop-down screen populated by the hospital pharmacy's formulary 22, accessed by the Monitoring Client 1 via the Monitoring Server 3. The 'PDR' button 29 may represent the physician's one-touch access to an in-hospital 22 or proprietary drug database 9 for detailed drug information. The physician can order the dose of medication, either directly or by accepting a default standard starting dose 30 provided by the Monitoring Client 1 via the Monitoring Server 3. The physician may also specify the maximum fluid infusion rate 31 for the infusion pump 7, in order to assist the pharmacist in preparing the proper concentration of the drug in a bag for infusion.

Figure 5:
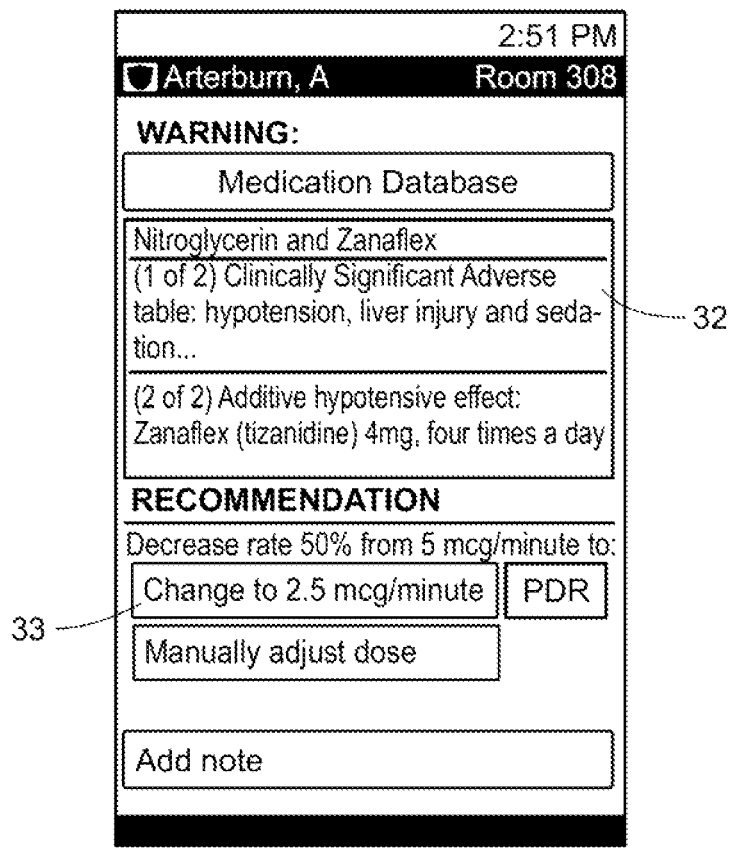
FIG. 5 is an illustration of a display screen on a health care provider's portable communications device, showing a risk profile associated with an ordered medication, and a suggested course of action, as generated by the Monitoring.

FIG. 5 shows an example of how the Patient Monitoring system can detect a risk of an adverse reaction after the physician has entered the prescription. The Monitoring Client 1 can compare the new medication 28 to the patient's existing medications and drug allergy list downloaded from the EHR 19. The Monitoring Server 3 preferably will have populated the appropriate patient-specific data into the Monitoring Client 1, and the Client 1 will be programmed to look up this information after the new medication order has been entered. The Monitoring Client 1 may be programmed to request a listing of significant adverse reactions and drug interactions associated with each of the patient's medications and the new medication 28 from the Monitoring Server 3. The Server 3, in turn can access a pharmacy database 22 or external database 9 for this information. If a potential drug interaction or adverse reaction common to an existing medication and the new medication 28 are detected, the Monitoring Client 1 may issue a warning 32 and transmit it to the ordering physician, as shown in FIG. 5. If the potential adverse reaction is due to an effect common to both the new medication and an existing medication, the Monitoring Client 1 may categorize this as a potentially additive adverse effect and issue a recommendation 33 to reduce the initial drug dose, for example, by 50%.

Figure 6:
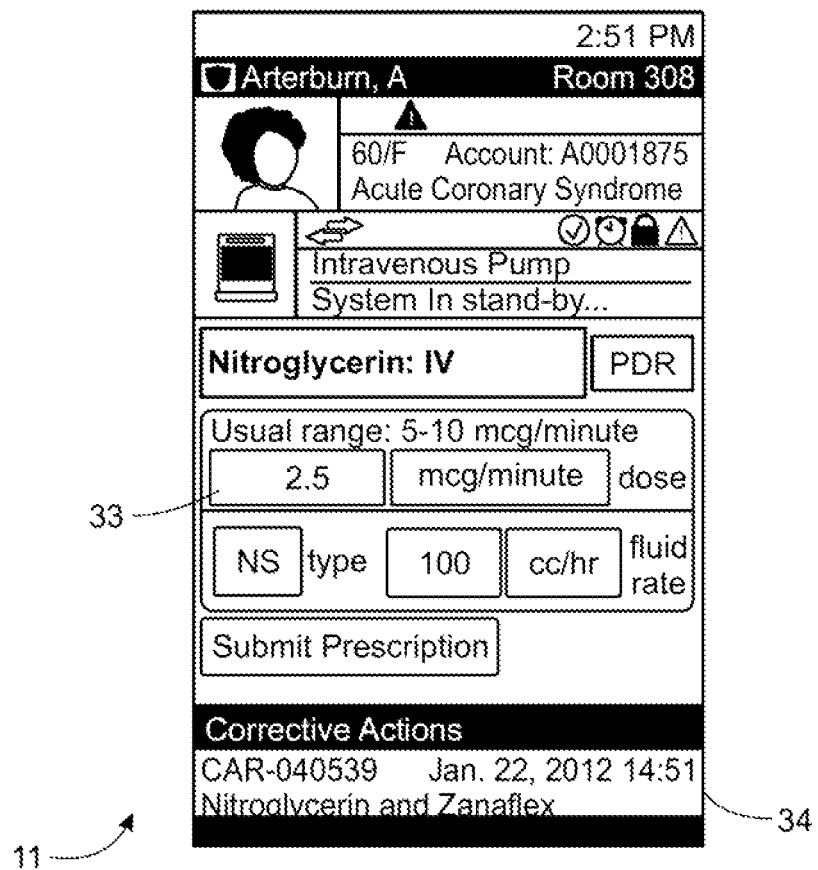
FIG. 6 is an illustration of a display screen on a health care provider's portable communications device, showing a medication prescription ready for submission by the ordering provider.

As shown in FIG. 6, the ordering physician has the option either to accept the recommendation 33 or edit the recommended dose to another value. In any event, the Monitoring Client 1 may generate and log a report 34 of the warning 32 and any corrective action 33, if any, taken by the physician, with the option for the physician to further edit the report before logging and entry into the patient's EHR 19.

Figure 7:
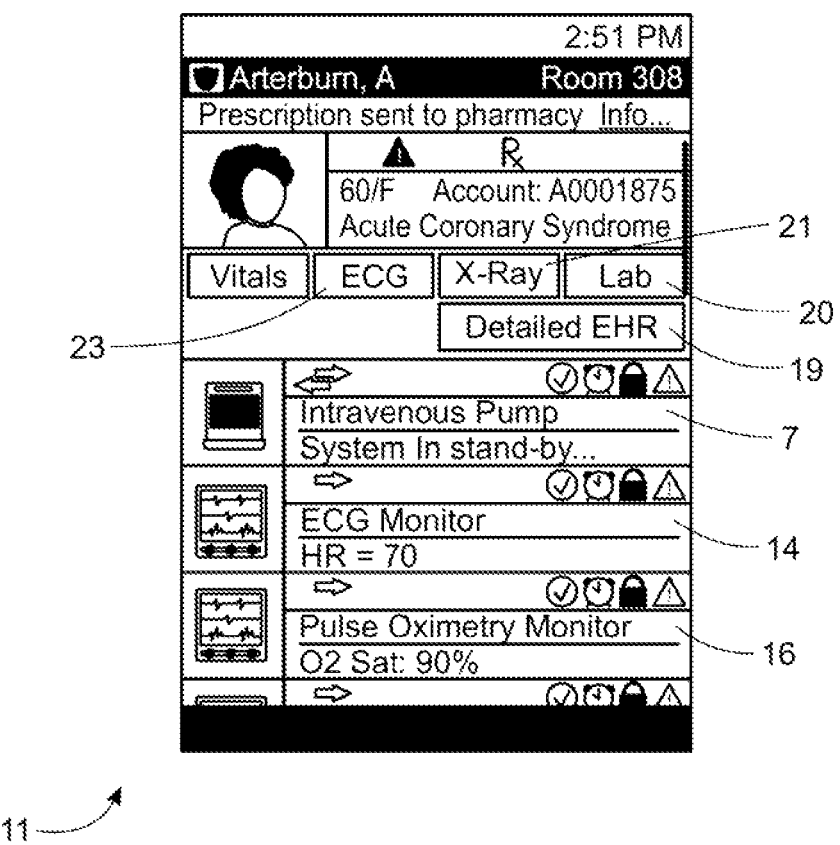
FIG. 7 is an illustration of a display screen on a health care provider's portable communications device, showing how the Monitoring system can display confirmation to the ordering provider that the prescription has been transmitted to the pharmacist.

Once the medication dosing is finally determined, the Monitoring Client 1 can forward the order to the communication devices of both the hospital pharmacist 6 and the patient's nurse 5. A report of the accomplishment of this task may then be transmitted back to the ordering physician 11, as shown in FIG. 7. The pharmacist can use the information provided by the ordering physician to mix an appropriate concentration of the medication in a solution bag. Both the medication vial and the solution bag may have identification tags, such as, e.g., bar code identifiers, that can be read into the pharmacist's communications device 6, and which can be verified as correct by the Monitoring Client 1 (using the pharmacy database 22 as accessed by the Monitoring Server 3). The pharmacist may then generate a unique identification label, such as a bar code label, to be permanently affixed to the medication bag, the code now being linked uniquely to the patient 2 for whom the medication 28 has been prepared. The identifying code on the label may be transmitted to the Monitoring Client 1 for later reconciliation when the nurse is about to administer the medication 28.

After the prepared medication 28 arrives to the patient's floor, the nurse can then prepare to administer it to the patient 2. In this exemplary scenario, the Monitoring Client 1 may include an input device such as a bar code reader, which the nurse can use to verify that the identifying code on the medication bag matches the identity of the patient 2 for whom it has been prescribed. If the identification matches the information entered into the Monitoring Client 1 by the pharmacist, the nurse may be cleared by the device 1 to hang the medication bag and initiate the infusion via the infusion pump 7. In an embodiment, the Monitoring Client 1 displays to the nurse the prescription, including the dose, the maximum fluid rate for the patient, the concentration of the drug in the bag, and the infusion rate for the pump (which can optionally be calculated by a processor in the Monitoring Client 1). With this information, the nurse has the ability to manually calculate and verify that the infusion rate set by the Monitoring Client 1 for the pump 7 is correct.

Network Connectivity Among System Components and Devices

A Monitoring Client device 1 can receive, process, and transmit information about a specific patient 2 to which it has been assigned or designated. The Monitoring Client 1 can most conveniently be attachable or dockable to an infusion pump 7, bed, or other device to which the patient 2 may be connected. The Monitoring Client 1 can be a hand-held device about the size of a wireless phone or tablet-style netbook, for example. Conveniently, it may have a touch-screen interface for use by the patient's provider. It may also be capable of providing output to a larger stationary display screen in the patient's room or at a nursing station 5 or other convenient location, either through a wired or wireless connection. Each Monitoring Client 1 may communicate with a central Monitoring Server 3, through which it can access patient data from the facility's EHR database 19, Laboratory database 20, Radiology database 21, Pharmacy database 22, or other databases in various other facility departments. In some cases, the Monitoring Client 1 can upload information it receives from patient monitoring systems 15-17 or from provider inputs to the patient's EHR 19 via the Monitoring Server 3. Monitoring Clients 1,4 may also receive information from databases outside of the facility through a Monitoring Server 3 having an internet connection 25. Various external databases 9 may thus be accessible, including various drug information databases and alert networks dealing with adverse medication-related events. The Monitoring Server 3 could be arranged, for example, to manage various levels of external database information helpful in keeping the Monitoring Client 1 contents as up-to-date as possible. This can be accomplished, for example, by comparing safety and drug information related to the patient as it becomes available, and prioritizing for updates/downloads on a data transfer schedule. The Monitoring Clients 1,4 may also communicate either directly or through the Monitoring Server 3 with portable communications devices 11 used by health care providers such as nurses, physicians and pharmacists. In some cases, these devices can have wired connections to the Monitoring Server 3 (if used, for example, in fixed locations such as hospital pharmacies or nursing stations). In other cases, a portable communications device 11 may communicate with the Monitoring Server 3 through VPN-based internet connections using a computer and a wired or wireless (such as, e.g., Bluetooth or WiFi 802.11) connection 13 with the device 11. Alternatively, a hand-held device 11 (such as a wireless smart-phone or tablet netbook) may communicate directly 12 with the facility's Monitoring Client 1 via a cellular telephone network.

The communications link between the Monitoring Clients 1,4 and the Monitoring Server 3 may exist via a Category-5 wired network if widely available in the facility, or via wireless transmission using one of a number of standards, linking all the patient-specific Monitoring Clients 1,4 with the central Monitoring Server 3. The server 3 may then serve as a relay for communications with other facility servers 8, with web-based servers 25, and with inside and outside portable communications devices 11 carried by medical care providers. A wireless network provides the additional functionality of being able to communicate with the Monitoring Server 3 no matter where in the facility the patient 2 may be.

One method of blanketing an entire facility with wireless coverage involves having the facility obtain a license for a private cell-phone network. It may obtain or lease one or more micro-cellular frequencies to provide for a local communications network throughout the facility. This arrangement can preserve communications when patients and their Monitoring Clients 1,4 are moved from one location to another within the facility, maintaining communications with a Monitoring Server 3, various in-hospital and out-of-hospital databases 8,25, and users at fixed stations 5,6 or with mobile smart-phone, laptop or tablet-type devices 11 either inside or outside the hospital. An advantage of this type of system is the level of security provided by a licensed cellular communications infrastructure. In addition, an active wireless system can monitor the intensity of use in an area and direct additional channel frequencies to that area as needed. However, the bandwidth capacity of the network may not allow for efficient transmission of large data files, such as those containing radiology images, for example.

Alternatively or additionally, a hospital may implement an internet or intranet based communications system, in which an 802.11 WiFi-type protocol is used for wireless communications between individual Monitoring Clients 1,4 and the main Monitoring Server 3. To ensure adequate signal reception throughout the facility, a broadband antenna may be mounted on the roof of the building to collect cell phone signals from local wireless phone companies. A fiber-optic or cable network may then distribute the signals throughout the facility. Alternatively, the Monitoring Server 3 may use the private cell-phone network mentioned above. Although this system may not be as secure as a micro-cell system, it may be capable of providing the data throughput to accommodate large files, such as, for example, radiology images stored in the Radiology database 21. Home or office-based users may be able to connect to the hospital server through VPN access using wired or fiber-optic cable, or a DSL phone line. Data encryption may be used to provide needed patient data security. In some applications it may be advantageous to implement an asymmetric bandwidth communications network in order to optimize infrastructure capabilities. An example of this would be using licensed cellular frequencies in the "upstream" direction from the Monitoring Client 1 to the Monitoring Server 3 and the unlicensed 802.11 WiFi frequencies in the "downstream" direction from the Monitoring Server 3 to the Monitoring Client 1. In this example the upstream bandwidth and data rate requirements are relatively small compared to the downstream requirements. In low priority upstream transmissions the Monitoring Client 1 may allow data to be sent over a more distributed and cost-efficient network, such as, for example, a ZigBee network.

Communications between various monitoring devices and the Monitoring Client 1 may be achieved in a cost effective manner using, for example, a ZigBee wireless mesh network. Exemplary monitoring devices include ECG monitors 14, blood pressure monitors 15, pulse oximeters/capnometers 16, thermometers, and weight scales, among others. A common characteristic of most of these devices is that they provide periodic readouts of a single or small number of parameters. An intra-hospital device communications system such as the wireless mesh network provides for low-power digital radio connectivity among devices, and may employ a widely available, license-free 2.4 GHz frequency band. High-level communications protocols may be employed to ensure data fidelity and security. It is highly scalable, allowing hundreds or thousands of devices to be used on a single self-forming, self-healing mesh network. Devices connected to the network may communicate with one another and serve as repeaters to transfer data efficiently. The advantages of this system are its relatively low cost, scalability and mobility for the patient being monitored. The wireless range for devices linked to the wireless mesh network can approach 70 meters from each node of the system inside a facility. A similar network may be used in providing a wireless link within the facility between portable communications devices 11 carried by health care providers and their assigned patients through the patients' Monitoring Clients 1,4.

In many cases, the information being transmitted to the Monitoring client 1 may include a single parameter value (such as, for example, blood pressure) and a time stamp. The Monitoring Client 1 can be programmed to determine whether the value is outside a predetermined range, record the value in the patient's EHR 19, and notify the appropriate care-giver via their communications device 11. Furthermore, the network may enable bidirectional communications, and may allow the Monitoring Client 1 to query 15 the monitoring device, instructing it 18 to take an unscheduled reading. This can be useful, for example, when an abnormal reading is received, and its authenticity needs to be verified. The Monitoring Client 1 may be programmed to request a repeat reading to verify the abnormal reading. In a further refinement, the Monitoring Client 1 may be programmed to interrupt or adjust the infusion pump 7 flow rate, depending on the value of the reading received from a monitoring device 14-17. For example, if the BP monitor 15 indicates a blood pressure below a pre-determined acceptable range, the Monitoring Client 1 may be programmed to instruct the infusion pump 7 to stop the infusion, and it can transmit an urgent notification 12 to the health care provider(s)' communications devices 11. In another embodiment, if the infusion pump 7 is capable of measuring the volume of fluid being delivered to the patient 2, a processor in the Monitoring Client 1 may track the cumulative volume delivered and estimate the amount of fluid remaining in the medication bag. (Alternatively, a processor in the Monitoring Client 1 or infusion pump 7 may calculate the volume delivered from the infusion rate and elapsed time of infusion). Once the estimated residual volume reaches a pre-determined amount, the Monitoring Client 1 may signal the infusion pump 7 to reduce its flow rate to keep the patient's IV access 35 from running dry. It may also send a notification to the nurse's communications device 11, recommending replenishment of the medication or solution.

The invention claimed is:
1. An electronic patient monitoring system comprising:
 an active wireless system including a micro-cellular network, the active wireless system including a monitor configured to detect intensity of use, the active wireless system configured to allocate channel frequencies in accordance with the detected intensity of use of an area by directing additional channel frequencies to the area;

a monitoring-server computer configured to retrieve physiological data of a patient from a database computer;
a tablet configured to operatively communicate with the monitoring-server computer to receive and locally store the physiological data of the patient received from the monitoring-server computer;
an infusion pump configured to infuse the patient with a medication; and
a smart phone in operative communication with the tablet, wherein the smart phone is configured to access the physiological data of the patient directly from the tablet without accessing the monitoring-server computer, wherein the monitoring-server computer, the tablet, and the smart phone are configured to communicate with each other over the micro-cellular network enabling the tablet to remain in communication with the monitoring-server computer while being mobile within a facility, wherein the smart phone is configured to display the physiological data of the patient next to a treatment order of the medication with an option to send the treatment order to the infusion pump and an option to view a reference of detailed information including information about the medication, the smart phone is configured to instruct the infusion pump to treat the patient with the medication via the micro-cellular network when the smart phone receives user input to treat the patient and the infusion pump is configured to execute treatment of the patient upon receipt of instruction from the smart phone, the smart phone configured to display the reference when the smart phone receives user input to view the reference,
wherein one of the tablet and the smart phone is configured, based at least in part on the physiological data of the patient, to alter a rate of infusion of the infusion pump by communicating a signal to the infusion pump as well as alert a health care provider.

2. The electronic patient monitoring system according to claim 1, wherein the smart phone communicates with the tablet using a wireless connection.

3. The electronic patient monitoring system according to claim 1, wherein the smart phone is configured to communicate with the tablet while outside of the facility having an associated patient located therein.

4. The electronic patient monitoring system according to claim 1, wherein the smart phone is configured to change at least one setting of the infusion pump based at least in part on data other than the physiological data of the patient and transmit the at least one setting to the tablet.

5. The electronic patient monitoring system according to claim 4, wherein the system is configured to communicate the at least one setting to the monitoring-server computer.

6. The electronic patient monitoring system according to claim 1, wherein the tablet is configured to store at least one of orders, medications, progress notes, and monitoring and treatment data from a device attached to a patient.

7. The electronic patient monitoring system according to claim 6, wherein the tablet is configured to periodically upload at least one of orders, medications, progress notes, and the monitoring and treatment data from the device attached to the patient to the database computer for permanent storage therein.

8. The electronic patient monitoring system according to claim 1, wherein the physiological data of the patient includes at least one of an age, a height, a weight, a current medication, a medication category, a medication allergy, and a medication sensitivity.

9. The electronic patient monitoring system according to claim 1, wherein the tablet is configured for assignment to a patient.

10. The electronic patient monitoring system according to claim 9, wherein the tablet is configured for assignment to the patient utilizing a unique patient identifier.

11. The electronic patient monitoring system according to claim 10, wherein the unique patient identifier is embedded on a bar code.

12. The electronic patient monitoring system according to claim 10, wherein the unique patient identifier is embedded within an RFID tag-embedded wrist band.

13. The electronic patient monitoring system according to claim 1, wherein the tablet is physically associated with the infusion pump.

14. The electronic patient monitoring system according to claim 1, further comprising a patient monitoring device configured to measure a physical characteristic of a patient, wherein the tablet receives the measure of the physical characteristic of the patient in real time.

15. The electronic patient monitoring system according to claim 1, wherein the tablet is adapted to determine if a new order meets predetermined criteria based upon a subset of the physiological data of the patient.

16. A system comprising:
a tablet configured to locally store physiological data of a patient;
a smart phone in operative communication with the tablet, wherein the smart phone is configured to access the physiological data of the patient directly from the tablet;
an infusion pump configured to infuse the patient with a medication; and
an active wireless network including a micro-cellular network, the active wireless network configured to provide communications between the tablet and the smart phone within a facility, the active wireless network including an intensity monitor configured to determine usage intensity of an area, the active wireless network allocating channel frequencies in accordance with the determined intensity by directing additional channel frequencies to the area;
wherein the smart phone is configured to display the physiological data of the patient next to a treatment order of the medication with an option to send the treatment order to the infusion pump and an option to view a physician's desk reference including detailed drug information, the smart phone is configured to instruct the infusion pump to treat the patient with the medication via the active wireless network when the smart phone receives user input to treat the patient and the infusion pump is configured to execute treatment of the patient upon receipt of instruction from the smart phone, the smart phone is configured to display the physician's desk reference when the smart phone receives user input to view the physician's desk reference,
wherein one of the tablet and the smart phone is configured, based at least in part on the physiological data of the patient, to alter a rate of infusion of the infusion pump by communicating a signal to the infusion pump as well as alert a health care provider.

17. The system according to claim 16, wherein the tablet is configured to be in physical proximity to an assigned patient.

18. The system according to claim 16, wherein the tablet is configured to retrieve and store the physiological data of the patient from a database computer over the micro-cellular network.

19. The system according to claim 18, wherein the database computer is an electronic health records database computer.

20. The system according to claim 18, wherein the smart phone is configured to access the physiological data of the patient without accessing the database computer.

21. The system according to claim 16, wherein the active wireless network includes a WIFI type network and the smart phone is configured to be in wireless communication with the tablet over at least one of the WIFI type network and the micro-cellular network.

22. The system according to claim 16, wherein the smart phone includes a touchscreen.

23. The system according to claim 22, wherein the smart phone is configured to provide one-touch access to a patient's medical information.

24. The system according to claim 16, wherein the tablet is physically associated with the infusion pump.

25. The system according to claim 16, wherein the tablet is configured to review information about a progress of treatment.

26. The system according to claim 16, wherein the smart phone is configured to communicate a change to a setting of the infusion pump directly to the tablet.

27. The system according to claim 16, wherein the tablet is configured to receive state parameters.

28. The system according to claim 27, wherein the tablet is configured to signal the infusion pump to at least one of halt infusion, alter the rate of infusion, and alert the health care provider when a state parameter of the state parameters is abnormal.

29. The system according to claim 28, wherein the tablet is configured to communicate the alert to the smart phone.

30. The system according to claim 16, wherein the smart phone is configured to show a risk profile associated with an ordered medication presented to assist a user with dosage, delivery or potential risks of the ordered medication.

31. The system according to claim 16, wherein the smart phone is configured to show a risk profile associated with a suggested course of action as generated by the tablet presented to assist a user with dosage, delivery or potential risks of an ordered medication.

32. The system according to claim 16, wherein the tablet is configured to access a database computer within the facility and access another database computer outside of the facility.

33. The system according to claim 16, wherein the physiological data of the patient includes at least one of an age, a height, a weight, a current medication, a medication category, a medication allergy, and a medication sensitivity.

* * * * *